United States Patent
Lee et al.

(10) Patent No.: US 12,343,701 B2
(45) Date of Patent: Jul. 1, 2025

(54) SUPERABSORBENT POLYMER AND PREPARATION METHOD THEREOF

(71) Applicant: LG Chem, Ltd., Seoul (KR)

(72) Inventors: Jin Woo Lee, Daejeon (KR); Jun Kyu Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 928 days.

(21) Appl. No.: 17/441,994

(22) PCT Filed: Sep. 7, 2020

(86) PCT No.: PCT/KR2020/012016
§ 371 (c)(1),
(2) Date: Sep. 22, 2021

(87) PCT Pub. No.: WO2021/066338
PCT Pub. Date: Apr. 8, 2021

(65) Prior Publication Data
US 2022/0203328 A1 Jun. 30, 2022

(30) Foreign Application Priority Data

Sep. 30, 2019 (KR) .................. 10-2019-0121181
Aug. 31, 2020 (KR) .................. 10-2020-0110242

(51) Int. Cl.
| | | |
|---|---|---|
| *C08J 3/12* | (2006.01) | |
| *A61L 15/24* | (2006.01) | |
| *A61L 15/44* | (2006.01) | |
| *A61L 15/60* | (2006.01) | |
| *A61L 26/00* | (2006.01) | |
| *B01J 20/26* | (2006.01) | |
| *B01J 20/28* | (2006.01) | |
| *B01J 20/30* | (2006.01) | |
| *C08J 3/24* | (2006.01) | |
| *C08K 5/00* | (2006.01) | |
| *C08K 5/098* | (2006.01) | |
| *C08K 5/138* | (2006.01) | |

(52) U.S. Cl.
CPC ............ *B01J 20/267* (2013.01); *A61L 15/24* (2013.01); *A61L 15/44* (2013.01); *A61L 15/60* (2013.01); *A61L 26/0014* (2013.01); *A61L 26/0061* (2013.01); *A61L 26/0066* (2013.01); *B01J 20/28016* (2013.01); *B01J 20/3021* (2013.01); *B01J 20/3078* (2013.01); *B01J 20/3085* (2013.01); *C08J 3/12* (2013.01); *C08J 3/245* (2013.01); *A61L 2300/404* (2013.01); *B01J 2220/44* (2013.01); *C08J 2333/02* (2013.01)

(58) Field of Classification Search
None
See application file for complete search history.

(56) References Cited

U.S. PATENT DOCUMENTS

| | | | |
|---|---|---|---|
| 5,322,896 A | 6/1994 | Jeda et al. | |
| 2004/0091558 A1 | 5/2004 | Lutz et al. | |
| 2004/0136954 A1 | 7/2004 | Grusby et al. | |
| 2005/0175679 A1* | 8/2005 | Moshman | A61P 25/08 |
| | | | 514/282 |
| 2009/0175966 A1 | 7/2009 | Lutz et al. | |
| 2009/0191289 A1 | 7/2009 | Lutz et al. | |
| 2009/0197803 A1 | 8/2009 | Grusby et al. | |
| 2010/0303869 A1* | 12/2010 | Azad | A61L 15/46 |
| | | | 514/721 |
| 2011/0009272 A1 | 1/2011 | Wattebled et al. | |
| 2012/0298915 A1 | 11/2012 | Okuda et al. | |
| 2014/0299815 A1 | 10/2014 | Ueda et al. | |
| 2015/0307667 A1 | 10/2015 | Wada et al. | |
| 2019/0046682 A1 | 2/2019 | Choi et al. | |
| 2019/0345600 A1 | 11/2019 | Koh et al. | |
| 2020/0122117 A1 | 4/2020 | Lee et al. | |
| 2020/0270441 A1 | 8/2020 | Lee et al. | |

(Continued)

FOREIGN PATENT DOCUMENTS

| | | |
|---|---|---|
| CN | 1688329 A | 10/2005 |
| CN | 101801427 A | 8/2010 |
| CN | 102898853 A | 1/2013 |

(Continued)

OTHER PUBLICATIONS

Schwalm, Reinhold, "UV Coatings: Basics, Recent Developments and New Applications", Elsevier, Dec. 2006, 3 pages.

(Continued)

*Primary Examiner* — Brian Gulledge
(74) *Attorney, Agent, or Firm* — Lerner David LLP

(57) ABSTRACT

Provided are a superabsorbent polymer capable of exhibiting improved bacterial growth-inhibitory property without deterioration in physical properties of the superabsorbent polymer, such as water retention capacity and absorbency under pressure, or without an increase in the generation of dust, and a preparation method thereof. The superabsorbent polymer may include a base polymer powder including a crosslinked polymer of water-soluble ethylenically unsaturated monomers including acidic groups, of which at least a part is neutralized; and a surface-crosslinked layer which is obtained by additionally crosslinking the crosslinked polymer via a surface crosslinking agent to be formed on the surface of the base polymer powder, wherein the crosslinked polymer of the base polymer powder or the surface-crosslinked layer includes an antimicrobial agent including an organic acid salt having an aromatic ring inside the crosslinked structure thereof.

15 Claims, No Drawings

(56) References Cited

U.S. PATENT DOCUMENTS

2020/0317872 A1  10/2020  Wada et al.

FOREIGN PATENT DOCUMENTS

| CN | 104664553 A | 6/2015 |
|---|---|---|
| EP | 0555692 A1 | 8/1993 |
| EP | 1187640 B1 | 9/2006 |
| EP | 3401354 A1 | 11/2018 |
| EP | 3564297 A1 | 11/2019 |
| EP | 3677628 A1 | 7/2020 |
| JP | H09030901 A | 2/1997 |
| JP | H09108317 A | 4/1997 |
| JP | 2000327926 A | 11/2000 |
| JP | 2010540004 A | 12/2010 |
| JP | 2011515511 A | 5/2011 |
| KR | 20100124349 A | 11/2010 |
| KR | 20150091363 A | 8/2015 |
| KR | 20150102578 A | 9/2015 |
| KR | 20180073335 A | 7/2018 |
| KR | 101948559 B1 | 2/2019 |
| KR | 20190060588 A | 6/2019 |
| WO | 2011099586 A1 | 8/2011 |
| WO | 2013073614 A1 | 5/2013 |

OTHER PUBLICATIONS

Odian, George, "Principles of Polymerization", John Wiley & Sons, 1981, p. 203.
International Search Report for PCT/KR2020/012016 mailed Jan. 4, 2021; 6 pages.
Third Party Observation for Application No. PCT/KR2020/012016 submitted Jan. 28, 2022, pp. 1-9.

* cited by examiner

SUPERABSORBENT POLYMER AND PREPARATION METHOD THEREOF

CROSS-REFERENCE TO RELATED APPLICATIONS

The present application is a national phase entry under 35 U.S.C. § 371 of International Application No. PCT/KR2020/012016, filed Sep. 7, 2020, which claims priority to Korean Patent Application No. 10-2019-0121181, filed Sep. 30, 2019, and Korean Patent Application No. 10-2020-0110242, filed on Aug. 31, 2020, the disclosures of which are hereby incorporated by reference herein in their entirety.

TECHNICAL FIELD

The present invention relates to a superabsorbent polymer capable of exhibiting improved bacterial growth-inhibitory property without deterioration in physical properties of the superabsorbent polymer, such as water retention capacity and absorbency under pressure, or without an increase in the generation of dust, and a preparation method thereof.

BACKGROUND

A superabsorbent polymer (SAP) is a synthetic polymer material capable of absorbing moisture of 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygienic products such as disposable diapers for children, etc., but also for water retaining soil products for gardening, water stop materials for the civil engineering and construction, sheets for raising seedling, fresh-keeping agents for food distribution fields, fomentation materials, or in the field of electrical insulation.

Such a superabsorbent polymer is most widely applied to hygienic products or disposable absorption products, such as disposable diapers for children or diapers for adults. Among them, in the case of being applied to diapers for adults, secondary odors resulting from bacterial growth gives consumers significant discomfort. In order to solve this problem, there have been attempts to introduce various bacterial growth-inhibiting components or deodorizing or antimicrobial functional components into superabsorbent polymers, etc.

However, in the attempts to introduce bacterial growth-inhibiting antimicrobial agents into superabsorbent polymers, it is not easy to select and introduce antimicrobial agents which exhibit excellent bacterial growth-inhibitory or deodorizing properties while being harmless to the human body, meeting economic efficiency, and not deteriorating basic physical properties of superabsorbent polymers.

For example, an attempt has been made to introduce an antimicrobial agent component containing antimicrobial metal ions such as silver and copper, e.g., copper oxide, into a superabsorbent polymer. These components containing antimicrobial metal ions destroy the cell walls of microorganisms such as bacteria, etc., and kill bacteria with enzymes that may cause odor in the superabsorbent polymer, thereby imparting deodorant properties. However, the components containing the metal ions are classified as a BIOCIDE material which is able to kill even microorganisms beneficial to the human body. For this reason, when the superabsorbent polymer is applied to hygienic products such as diapers for children or adults, etc., introduction of the antimicrobial agent component containing metal ions is excluded as much as possible.

Meanwhile, when a bacterial growth-inhibiting antimicrobial agent is introduced into superabsorbent polymers, a method of blending a small amount of the antimicrobial agent with the superabsorbent polymers has been mainly applied. However, when this blending method is applied, it is practically difficult to uniformly maintain the bacterial growth-inhibitory properties over time. Moreover, such a blending method may cause uneven coating and desorption of the antimicrobial agent component during a process of blending the superabsorbent polymer with the antimicrobial agent or a process of using the superabsorbent polymer. As a result, it is necessary to install a new facility for blending the antimicrobial agent, and there are also disadvantages such as generation of a large amount of dust during a process of using the superabsorbent polymer.

Accordingly, there is a continuous demand for the development of a technology related to a superabsorbent polymer capable of uniformly maintaining bacterial growth-inhibitory and deodorizing properties for a long time without introducing metal ion-containing components while suppressing generation of dust without deteriorating the basic properties of the superabsorbent polymer.

Technical Problem

Accordingly, there are provided a superabsorbent polymer capable of uniformly maintaining excellent bacterial growth-inhibitory and deodorizing properties for a long time without introducing components harmful to the human body while maintaining basic physical properties, such as water retention capacity, absorbency under pressure, etc., and suppressing an increase in the generation of dust, and a preparation method thereof.

Further, there is provided a hygienic product which includes the superabsorbent polymer to uniformly exhibit the excellent bacterial growth-inhibitory and deodorizing properties for a long time while suppressing the generation of dust and maintaining excellent basic absorption properties.

Technical Solution

There is provided a superabsorbent polymer including:
a base polymer powder including a crosslinked polymer of water-soluble ethylenically unsaturated monomers including acidic groups, of which at least a part is neutralized; and
a surface-crosslinked layer which is obtained by additionally crosslinking the crosslinked polymer via a surface crosslinking agent to be formed on the surface of the base polymer powder,
wherein the crosslinked polymer of the base polymer powder or the surface-crosslinked layer includes an antimicrobial agent including an organic acid salt having an aromatic ring inside the crosslinked structure thereof.

Further, there is provided a method of preparing the superabsorbent polymer, the method including the steps of:
performing crosslinking polymerization of water-soluble ethylenically unsaturated monomers including acidic groups, of which at least a part is neutralized, in the presence of an internal crosslinking agent to form a water-containing gel polymer;

drying, pulverizing, and size-sorting the water-containing gel polymer to form a base polymer powder; and performing additional crosslinking of the base polymer powder by heat treatment in the presence of a surface crosslinking agent, wherein the step of forming the water-containing gel polymer or the step of performing additional crosslinking is performed in the presence of an antimicrobial agent containing an organic acid salt having an aromatic ring.

Further, there is provided a hygienic product including the superabsorbent polymer.

Effect of the Invention

A superabsorbent polymer of the present invention may include a particular antimicrobial agent containing no metal ions, etc., thereby exhibiting excellent bacterial growth-inhibitory and deodorizing properties of selectively inhibiting proliferation of bacteria which are harmful to the human body and cause secondary odors.

Further, the particular antimicrobial agent is applied to the superabsorbent polymer during crosslinking polymerization or surface crosslinking, and is tightly fixed inside the crosslinked polymer constituting the base polymer powder or the surface-crosslinked layer, thereby uniformly exhibiting excellent bacterial growth-inhibitory and deodorizing properties for a long time, and maintaining excellent water retention capacity and absorbency under pressure without deterioration in the physical properties due to addition of the antimicrobial agent. Additionally, since the antimicrobial agent is fixed inside the crosslinked structure of the superabsorbent polymer, it is also possible to solve the disadvantage of generating a large amount of dust due to addition of the antimicrobial agent.

Accordingly, the superabsorbent polymer may be very preferably applied to a variety of hygienic products, particularly, diapers for adults having a problem of secondary odors, etc.

DETAILED DESCRIPTION OF THE EMBODIMENTS

The terms used in this description are just for explaining exemplary embodiments and it is not intended to restrict the present invention. The singular expression may include the plural expression unless it is differently expressed contextually. It must be understood that the term "include", "equip", or "have" in the present description is only used for designating the existence of characteristics taken effect, steps, components, or combinations thereof, and do not exclude the existence or the possibility of addition of one or more different characteristics, steps, components, or combinations thereof beforehand.

The present invention may be variously modified and have various forms, and specific examples of the present invention are explained in this description. However, it is not intended to limit the present invention to the specific examples and it must be understood that the present invention includes every modifications, equivalents, or replacements included in the spirit and technical scope of the present invention.

Hereinafter, a superabsorbent polymer and a preparation method thereof will be described in more detail according to specific embodiments of the present invention.

A superabsorbent polymer according to one embodiment of the present invention may include a base polymer powder including a crosslinked polymer of water-soluble ethylenically unsaturated monomers including acidic groups, of which at least a part is neutralized; and a surface-crosslinked layer which is obtained by additionally crosslinking the crosslinked polymer via a surface crosslinking agent to be formed on the surface of the base polymer powder, wherein the crosslinked polymer of the base polymer powder or the surface-crosslinked layer includes an antimicrobial agent including an organic acid salt having an aromatic ring inside the crosslinked structure thereof.

The present inventors have continuously studied antimicrobial agent components preferably applicable to a superabsorbent polymer, instead of antimicrobial agent components containing antimicrobial metal ions such as silver, copper, etc. As a result of the continuous studies, they found that when an antimicrobial agent component including an organic acid salt having an aromatic ring is introduced into the superabsorbent polymer, the superabsorbent polymer may be provided with excellent bacterial growth-inhibitory and deodorizing properties of inhibiting proliferation of odor-causing bacteria existing in the human skin, without deteriorating basic properties of the superabsorbent polymer, such as water retention capacity, absorbency under pressure, etc.

In particular, an organic acid salt having an aromatic ring, for example, sodium benzoate, which is a component harmless to the human body enough to be used in foods or cosmetics, and safe to use, does not correspond to BIOCIDE materials, and is able to solve the problems of the existing antibacterial agents containing metal ions.

Furthermore, the antimicrobial agent component including an organic acid salt having an aromatic ring is applied to the superabsorbent polymer of one embodiment during crosslinking polymerization or surface crosslinking, and is tightly fixed and included inside or on the surface of the crosslinked polymer constituting the base polymer powder or surface-crosslinked layer. Therefore, even though a separate facility for blending is not used, the antimicrobial agent component may be uniformly included in the superabsorbent polymer without desorption, and the disadvantage of generating a large amount of dust during use of the superabsorbent polymer may also be suppressed.

Therefore, the superabsorbent polymer of one embodiment may uniformly exhibit excellent bacterial growth-inhibitory and deodorizing properties for a long time, and may maintain excellent water retention capacity and absorbency under pressure without deterioration of physical properties due to addition of the antimicrobial agent. As a result, the superabsorbent polymer of one embodiment may be very preferably applied to a variety of hygienic products, particularly, diapers for adults having a problem of secondary odors, etc.

Meanwhile, in the superabsorbent polymer of one embodiment, a metal salt of an organic acid salt having an aromatic ring may be used as the organic acid salt having an aromatic ring. In view of the excellent bacterial growth-inhibitory property thereof, a sodium (Na) salt or a zinc (Zn) salt of an organic acid having an aromatic ring may be used. More specific examples of the organic acid salt having an aromatic ring may include sodium benzoate or zinc benzoate.

The organic acid salt having an aromatic ring may be included in an amount of 0.1 part by weight to 5 parts by weight, 0.3 parts by weight to 4 parts by weight, or 0.4 parts by weight to 3 parts by weight, based on 100 parts by weight of the base polymer powder. When the amount of the organic acid salt having an aromatic ring is too small, it is difficult to exhibit appropriate bacterial growth-inhibitory and deodorizing properties, and on the contrary, when the amount thereof is too large, basic properties of the superabsorbent polymer, such as water retention capacity, etc., may be deteriorated.

Further, the antimicrobial agent included in the surface-crosslinked layer may further include ethylenediaminetetraacetic acid (EDTA) or an alkali metal salt thereof, in addition to the organic acid salt having an aromatic ring. These components may chelate nutrients of secondary odor-causing microbes, such as bacteria, etc., thereby inhibiting metabolisms of the bacteria. As a result, the superabsorbent polymer further including the same may exhibit more improved bacterial growth-inhibitory and deodorizing properties.

The kind of EDTA or an alkali metal salt thereof is not particularly limited, and any component known to be added to the superabsorbent polymer as the chelating agent, etc., for example, EDTA-2Na or EDTA-4Na may be used.

EDTA or an alkali metal salt thereof may be included in an amount of 0.1 part by weight to 3 parts by weight, 0.3 parts by weight to 2 parts by weight, or 0.4 parts by weight to 1 part by weight, based on 100 parts by weight of the base polymer powder. By additionally using such EDTA or an alkali metal salt thereof, excellent antibacterial and deodorizing properties may be exhibited by further suppressing the growth rate of odor-causing bacteria. However, when the amount of EDTA or an alkali metal salt thereof is too large, it may cause a decrease in the absorption properties of the superabsorbent polymer, which is not preferable.

Meanwhile, the above-described superabsorbent polymer of one embodiment may have a common superabsorbent polymer structure, except that the antimicrobial agent component is included inside the internal crosslinked structure of the crosslinked polymer which constitutes the base polymer powder or inside the crosslinked structure of the surface-crosslinked layer. For example, the superabsorbent polymer may have a structure including the base polymer powder including the crosslinked polymer of water-soluble ethylenically unsaturated monomers including acidic groups, of which at least a part is neutralized; and the surface-crosslinked layer which is obtained by additionally crosslinking the crosslinked polymer via a surface crosslinking agent to be formed on the surface of the base polymer powder.

In this regard, as the water-soluble ethylenically unsaturated monomer, any monomer commonly used in the superabsorbent polymers may be used without particular limitation. Here, any one or more monomers selected from the group consisting of anionic monomers and salts thereof, nonionic hydrophilic monomers, and amino group-containing unsaturated monomers and quaternarized products thereof may be used.

Specifically, one or more selected from the group consisting of anionic monomers such as (meth)acrylic acid, maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, and salts thereof; nonionic hydrophilic monomers such as (meth) acrylamide, N-substituted (meth)acrylate, 2-hydroxyethyl (meth)acrylate, 2-hydroxypropyl(meth)acrylate, methoxypolyethyleneglycol(meth)acrylate, or polyethyleneglycol (meth)acrylate; and amino group-containing unsaturated monomers such as (N,N)-dimethylaminoethyl(meth)acrylate or (N,N)-dimethylaminopropyl(meth)acrylamide, and quaternarized products thereof may be used.

More preferably, acrylic acid or a salt thereof, for example, acrylic acid or an alkali metal salt thereof such as a sodium salt thereof may be used. When these monomers are used, it is possible to prepare a superabsorbent polymer having superior physical properties. When an alkali metal salt of acrylic acid is used as a monomer, acrylic acid may be used after being at least partially neutralized with a basic compound such as caustic soda (NaOH).

Further, the base polymer powder may have a fine powder form including the crosslinked polymer which is obtained by crosslinking the monomers via an internal crosslinking agent.

As the internal crosslinking agent, a crosslinking agent having one or more functional groups reactable with a water-soluble substituent of the water-soluble ethylenically unsaturated monomer and one or more soluble ethylenically unsaturated groups; or a crosslinking agent having two or more functional groups reactable with a water-soluble substituent of the monomer and/or a water-soluble substituent formed by hydrolysis of the monomer may be used.

Specific examples of the internal crosslinking agent may include one or more selected from the group consisting of bisacrylamide having 8 to 12 carbon atoms, bismethacrylamide, poly(meth)acrylate of a polyol having 2 to 10 carbon atoms, or poly(meth)allyl ether of a polyol having 2 to 10 carbon atoms. More specific examples thereof may include N,N'-methylene bis(meth)acrylate, ethyleneoxy(meth)acrylate, polyethyleneoxy (meth)acrylate, propyleneoxy(meth) acrylate, glycerin diacrylate, glycerin triacrylate, tri methyloltriacrylate, triallylamine, triarylcyanurate, triallylisocyanate, polyethylene glycol, diethylene glycol, and propylene glycol.

Further, the base polymer powder may have a fine powder form having a particle size of 150 μm to 850 μm.

Meanwhile, the superabsorbent polymer may include the surface-crosslinked layer which is obtained by additionally crosslinking the crosslinked polymer of the base polymer powder via a surface crosslinking agent to be formed on the surface of the base polymer powder.

Examples of the surface crosslinking agent may include diol compounds, alkylene carbonate compounds, polyvalent epoxy compounds, etc., and more specific examples thereof may include 1,3-propanediol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, ethylene carbonate, propylene carbonate, glycerol carbonate, diglycidyl ether of alkylene glycol, such as ethylene glycol diglycidyl ether, etc. In addition, any polyvalent compound known to be applicable as the surface crosslinking agent of superabsorbent polymers may be used without any limitation.

The above-described superabsorbent polymer of one embodiment includes the antimicrobial agent component, such as an organic acid salt having an aromatic ring, for example, in an aqueous monomer solution or a surface crosslinking solution to form the crosslinked polymer or the surface-crosslinked layer of the base polymer powder, and thus the antimicrobial agent component is physically or chemically fixed or bonded to the inside or the surface of the internal crosslinked structure of the crosslinked polymer or the additional crosslinked structure of the surface-crosslinked layer. As a result, unlike existing blending, non-uniform application of the antimicrobial agent component, and desorption or separation thereof during transportation do not occur, and the antimicrobial agent component is uniformly included throughout the structure, and thus excellent bacterial growth-inhibitory and deodorizing properties may be stably displayed for a long time. In addition, when the superabsorbent polymer is used, generation of dust derived from the antimicrobial agent component may also be greatly reduced.

As demonstrated in Experimental Examples described below, such excellent bacterial growth-inhibitory property may be supported by having a high bacterial inhibition rate (*Escherichia coli*; ATCC25922) of 75% or more, or 80% or more, or 90% to 100%, represented by the following Equation 1:

Bacterial inhibition rate=[1−{CFU(12 h)/CFUcontrol (12 h)}]*100(%)  [Equation 1]

in Equation 1, CFU (12 h) represents the number of individuals of proliferated bacteria per unit volume of synthetic urine (CFU/ml), which was obtained by adding the superabsorbent polymer to the synthetic urine inoculated with bacteria of *Escherichia coli* (ATCC 25922), and then incubating for 12 hours at 35° C., and CFUcontrol (12 h) represents the number of individuals of proliferated bacteria per unit volume of synthetic urine (CFU/ml), which was obtained by incubating synthetic urine inoculated with bacteria of *Escherichia coli* (ATCC 25922), without the superabsorbent polymer, under the same conditions.

Further, the superabsorbent polymer may exhibit excellent dust-inhibitory property, and as demonstrated in Experimental Examples described below, the dust-inhibitory property may be supported by having a low dust number of 1 to 5, or 1.2 to 3.5, or 1.5 to 2.5, as calculated according to the following Equation 2 from the results of a laser dust meter:

Dust number=Max value+30 sec. value  [Equation 2]

in Equation 2, Max value represents the value which is measured at the maximum DUST value when the superabsorbent polymer is dropped into the inlet of the laser dust meter, and 30 sec. value represents the value which is measured for 30 seconds after the Max value is displayed.

Meanwhile, the above-described superabsorbent polymer of one embodiment may be obtained by drying, pulverizing, size-sorting, and surface-crosslinking the water-containing gel polymer which is obtained by performing thermal polymerization or photo-polymerization of a monomer composition including the water-soluble ethylenically unsaturated monomers and a polymerization initiator. If necessary, a process of reassembling fine powder may be further performed.

More specifically, a method of preparing the superabsorbent polymer may include the steps of:

performing crosslinking polymerization of water-soluble ethylenically unsaturated monomers including acidic groups, of which at least a part is neutralized, in the presence of an internal crosslinking agent to form a water-containing gel polymer;

drying, pulverizing, and size-sorting the water-containing gel polymer to form a base polymer powder; and performing additional crosslinking of the base polymer powder by heat treatment in the presence of a surface crosslinking agent, wherein the step of forming the water-containing gel polymer or the step of performing additional crosslinking is performed in the presence of the antimicrobial agent containing an organic acid salt having an aromatic ring.

In one specific embodiment, in the step of forming the water-containing gel polymer, the crosslinking polymerization of a monomer aqueous solution including the water-soluble ethylenically unsaturated monomers, the polymerization initiator, the internal crosslinking agent, and the antimicrobial agent may be performed. As a result, the superabsorbent polymer of one embodiment, in which the antimicrobial agent is included inside the crosslinked structure of the crosslinked polymer constituting the base polymer powder, may be obtained.

In another specific embodiment, the step of performing additional crosslinking may be performed by using a surface crosslinking solution including the surface crosslinking agent and the antimicrobial agent containing the organic acid salt having an aromatic ring. As a result, the superabsorbent polymer of one embodiment, in which the antimicrobial agent is included inside the additional crosslinked structure of the surface-crosslinked layer, may be obtained.

As described, in the step of performing the crosslinking polymerization to form the water-containing gel polymer and the base polymer powder or in the step of performing additional crosslinking to form the surface-crosslinked layer, since the process of preparing the superabsorbent polymer is performed by including the antimicrobial agent component in the monomer aqueous solution or the surface crosslinking solution, the antimicrobial agent component may be introduced into the superabsorbent polymer through the common process of preparing superabsorbent polymers without additional facility for blending, etc. Furthermore, as described above, the antimicrobial agent component is tightly fixed inside the surface-crosslinked layer to prevent desorption or uneven coating thereof, and to allow the superabsorbent polymer to uniformly maintain excellent bacterial growth-inhibitory and deodorizing properties for a long time. Additionally, it is possible to avoid a problem of generating dust due to the antimicrobial agent component during use of the superabsorbent polymer.

Meanwhile, since the kinds of respective components applicable in the preparation method, i.e., the monomer, the internal crosslinking agent, the surface crosslinking agent, and the antimicrobial agent, have been already described in detail with regard to the superabsorbent polymer of one embodiment, additional descriptions thereof will be omitted.

Further, the amount of each antimicrobial agent component used in the preparation method may also correspond to the content of each antimicrobial agent component as described above. However, when the antimicrobial agent component is used during the crosslinking polymerization, it is used in the above-described range of the content, based on 100 parts by weight of the water-soluble ethylenically unsaturated monomers, and even in the final superabsorbent polymer, its amount may be adjusted such that it is included in the same range of the content, based on 100 parts by weight of the base polymer powder.

Additional description of the content range of the antimicrobial agent will be omitted, and the description will focus on the process of preparing the superabsorbent polymer.

In the method of preparing the superabsorbent polymer, the crosslinking polymerization of the water-soluble ethylenically unsaturated monomers including acidic groups, of which at least a part is neutralized, may be performed in the presence of an internal crosslinking agent to form the water-containing gel polymer. To this end, a monomer aqueous solution including the monomer, the polymerization initiator, the internal crosslinking agent, and an aqueous solvent may be used, and additionally, the above-described antimicrobial agent may be further included in the monomer aqueous solution.

In this regard, as the polymerization initiator, those generally used in the preparation of superabsorbent polymers may be used without particular limitation.

Specifically, the polymerization initiator may be a thermal polymerization initiator or a photo-polymerization initiator by UV irradiation, depending on the polymerization method. However, even in the case of using the photo-polymerization method, since a certain amount of heat is generated by the ultraviolet irradiation or the like, and a certain degree of heat is also generated according to the progress of the exothermic polymerization reaction, a thermal polymerization initiator may be additionally included. The photo-polymerization initiator may be used without any limitation in view of constitution, as long as it is a compound capable of forming a radical by light such as UV ray.

The photo-polymerization initiator may include, for example, one or more initiators selected from the group consisting of benzoin ether, dialkyl acetophenone, hydroxyl alkylketone, phenyl glyoxylate, benzyl dimethyl ketal, acyl phosphine, and α-aminoketone. Meanwhile, specific examples of the acyl phosphine may include diphenyl(2,4,6-trimethylbenzoyl)phosphine oxide, phenylbis(2,4,6-trimethylbenzoyl)phosphine oxide, ethyl (2,4,6-trimethylbenzoyl)phenylphosphinate, etc. More various photo-polymerization initiators are well disclosed in "UV Coatings: Basics, Recent Developments and New Application (Elsevier, 2007)" written by Reinhold Schwalm, p 115, however the photo-polymerization initiator is not limited to the above-described examples.

The photo-polymerization initiator may be included at a concentration of about 0.0001% by weight to about 2.0% by weight with respect to the monomer aqueous solution. When the concentration of the photo-polymerization initiator is too low, the polymerization rate may become slow, and when the concentration of the photo-polymerization initiator is too high, a molecular weight of the superabsorbent polymer becomes small and its physical properties may become uneven.

Further, as the thermal polymerization initiator, one or more initiators selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), etc., and examples of the azo-based initiator may include 2,2-azobis-(2-amidinopropane) dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, 4,4-azobis-(4-cyanovaleric acid), etc. More various thermal polymerization initiators are well disclosed in 'Principle of Polymerization (Wiley, 1981)' written by Odian, p 203, however, the thermal polymerization initiator is not limited to the above-described examples.

The thermal polymerization initiator may be included at a concentration of about 0.001% by weight to about 2.0% by weight with respect to the monomer aqueous solution. When the concentration of the thermal polymerization initiator is too low, additional thermal polymerization hardly occurs, and thus effects due to the addition of the thermal polymerization initiator may be insignificant, and when the concentration of the thermal polymerization initiator is too high, the molecular weight of the superabsorbent polymer becomes small and the physical properties may become uneven.

When the photo-polymerization initiator and the thermal polymerization initiator are used together, the thermal polymerization initiator may be lastly added to the monomer aqueous solution, immediately before initiation of the polymerization. In this regard, the aqueous solution of the antimicrobial agent may be mixed with the thermal polymerization initiator, and then added to the monomer aqueous solution.

Further, in the preparation method, the monomer aqueous solution of the superabsorbent polymer may further include additives such as a thickener, a plasticizer, a preservation stabilizer, an antioxidant, etc., if necessary.

Meanwhile, the method of forming the water-containing gel polymer by thermal polymerization or photo-polymerization of the monomer aqueous solution is also not particularly limited in view of constitution, as long as it is a polymerization method commonly used.

Specifically, the polymerization method is largely classified into the thermal polymerization and the photo-polymerization according to a polymerization energy source. The thermal polymerization may be commonly carried out in a reactor like a kneader equipped with agitating spindles whereas the photo-polymerization may be carried out in a reactor equipped with a movable conveyor belt. The above-described polymerization method is an example only, and the present invention is not limited to the above-described polymerization methods.

The water-containing gel polymer obtained by the above-mentioned method may generally have a water content of about 40% by weight to about 80% by weight. Meanwhile, the "water content" as used herein means a weight occupied by water with respect to the total weight of the water-containing gel polymer, which may be a value obtained by subtracting the weight of the dried polymer from the weight of the water-containing gel polymer. Specifically, the water content may be defined as a value calculated by measuring the weight loss due to evaporation of moisture in the polymer during the process of drying by raising the temperature of the polymer through infrared heating. At this time, the water content is measured under the drying conditions determined as follows: the drying temperature is increased from room temperature to about 180° C. and then the temperature is maintained at 180° C., and the total drying time is set to 20 minutes, including 5 minutes for the temperature rising step.

Next, the obtained water-containing gel polymer is dried. If necessary, coarse pulverization may be further performed before drying, in order to increase efficiency of the drying step.

In this regard, a pulverizer used here is not limited by its configuration, and specifically, it may include any one selected from the group consisting of a vertical pulverizer, a turbo cutter, a turbo grinder, a rotary cutter mill, a cutter mill, a disc mill, a shred crusher, a crusher, a chopper, and a disc cutter, but is not limited to the above-described examples.

In this regard, the coarse pulverization may be carried out such that the particle diameter of the water-containing gel polymer becomes about 2 mm to about 10 mm.

The water-containing gel polymer coarsely pulverized as above or the water-containing gel polymer immediately after polymerization without the coarse pulverizing step is dried.

In the drying step, any drying method may be selected and used without limitation in view of constitution, as long as it is commonly used in the process of drying the water-containing gel polymer. Specifically, the drying step may be carried out by a method such as hot air supply, infrared irradiation, microwave irradiation, or ultraviolet irradiation. When the drying step as above is finished, the water content of the polymer may be 0.1% by weight to 10% by weight.

Next, the dried polymer obtained through the drying step is pulverized.

The polymer powder obtained through the pulverizing step may have a particle diameter of about 150 μm to about 850 μm. Specific examples of a pulverizer which may be used to achieve the above particle diameter may include a pin mill, a hammer mill, a screw mill, a roll mill, a disc mill, a jog mill, etc., but the present invention is not limited to the above-described examples.

In order to manage the physical properties of the superabsorbent polymer powder that is finally commercialized after the pulverization step, the polymer powder obtained after the pulverization is generally size-sorted depending on the particle diameter. Preferably, the polymer powder is sorted into a polymer having a particle diameter of 150 μm to 850 μm.

According to one exemplary embodiment of the present invention, the step of surface-crosslinking the pulverized and size-sorted polymer may be further performed.

The above step is a step of forming a surface-crosslinked layer by performing additional crosslinking using a surface crosslinking agent in order to increase the surface crosslinking density of the base polymer powder, wherein unsaturated bonds of water-soluble ethylenically unsaturated monomers remaining on the surface without crosslinking are further crosslinked by the surface crosslinking agent, thereby forming a superabsorbent polymer having a high surface crosslinking density. The surface crosslinking density, i.e., the external crosslinking density, is increased by this heat treatment process, whereas the internal crosslinking density does not change, and as a result, the superabsorbent polymer having the surface-crosslinked layer formed thereon has a structure having a higher crosslinking density outside than inside.

This surface-crosslinking step may be performed, as described above, by using the surface crosslinking solution including the surface crosslinking agent, the antimicrobial agent including the organic acid salt having an aromatic ring, and optionally, EDTA or an alkali metal salt thereof, and the aqueous solvent.

The surface crosslinking agent may be used in an amount of 0.001 parts by weight to 2 parts by weight, based on 100 parts by weight of the base polymer powder. For example, the surface crosslinking agent may be used in an amount of 0.005 parts by weight or more, 0.01 part by weight or more, or 0.02 parts by weight or more, and 1.5 parts by weight or less, or 1 part by weight or less, based on 100 parts by weight of the base polymer powder. By controlling the amount of the surface crosslinking agent in the above-described range, a superabsorbent polymer having excellent physical properties such as absorption performance and liquid permeability may be prepared.

Further, with regard to a method of mixing the surface crosslinking solution with the base polymer powder, there is no limitation in view of constitution. For example, a method of adding and mixing the surface crosslinking solution and the base polymer powder in a reactor, a method of spraying the surface crosslinking solution onto the base polymer powder, or a method of continuously feeding the base polymer powder and the surface crosslinking solution to a mixer which is continuously operated may be used.

Further, the surface crosslinking process may be carried out at a temperature of about 80° C. to about 250° C. More specifically, the surface crosslinking process may be carried out at about 100° C. to about 220° C. or about 120° C. to about 200° C. for 20 minutes to 2 hours, or 40 minutes to 80 minutes. When the above-described surface crosslinking conditions are satisfied, the surface of the base polymer powder is sufficiently crosslinked, and absorbency under pressure or liquid permeability may be increased.

A means for raising the temperature for surface crosslinking reaction is not particularly limited. Heating may be performed by providing a heating medium or by directly providing a heat source. In this regard, the kind of the heating medium applicable may be a hot fluid such as steam, hot air, hot oil or the like, but the present invention is not limited thereto. The temperature of the heating medium to be provided may be properly controlled, taking into consideration the means of the heating medium, the heating rate, and the target temperature. Meanwhile, as the heat source to be directly provided, an electric heater or a gas heater may be used, but the present invention is not limited to these examples.

Meanwhile, through the process exemplarily described above, when the surface crosslinking process is performed, a superabsorbent polymer may be prepared and provided. This superabsorbent polymer includes the above-described specific antimicrobial agent component which is tightly fixed inside the surface-crosslinked layer, thereby exhibiting excellent bacterial growth-inhibitory and deodorizing properties, and maintaining excellent basic absorption properties.

Accordingly, such superabsorbent polymer may be preferably included and used in various hygienic products, for example, disposable diapers for children, diapers for adults, or sanitary napkins. In particular, it may be very preferably applied to diapers for adults having a problem of secondary odors, etc., which is caused by bacterial growth.

These hygienic products may follow the configuration of common hygienic products, except that the superabsorbent polymer of one embodiment is included in an absorber.

Hereinafter, the actions and effects of the present invention will be described in more detail with reference to specific exemplary embodiments of the present invention. However, these exemplary embodiments are for illustrative purposes only, and the scope of the present invention is not intended to be limited thereby.

EXAMPLE

Examples and Comparative Examples: Preparation of Superabsorbent Polymer

Comparative Example 1

To a 3-L glass reactor equipped with a stirrer and a thermometer, 484 g of acrylic acid, 2100 ppmw of polyethylene glycol diacrylate (PEGDA 400, Mw=400) as an internal crosslinking agent, and 80 ppmw of diphenyl(2,4,6-trimethylbenzoyl)-phosphine oxide as a photoinitiator were added and dissolved, and then 643 g of 31.5 wt % sodium hydroxide solution was added to prepare a water-soluble unsaturated monomer aqueous solution (degree of neutralization: 70 mol %; solid content: 45.8% by weight).

When the temperature of the water-soluble unsaturated monomer aqueous solution increased to 40° C. due to the heat of neutralization, the mixture was put in a container containing 2400 ppmw of sodium persulfate (SPS) which is a thermal polymerization initiator, and UV polymerization was allowed by ultraviolet ray irradiation for 1 minute (UV dose: 10 mV/cm$^2$), and aging was performed by heating in an oven at 80° C. for 120 seconds to obtain a water-containing gel polymer sheet.

The obtained water-containing gel polymer sheet was passed through a chopper having a hole size of 16 mm to prepare crumbs. Then, the crumbs were dried in an oven capable of shifting airflow up and down. The crumbs were uniformly dried by flowing hot air at 185° C. from the bottom to the top for 15 minutes and from the top to the bottom for 15 minutes, such that a water content of the dry product became 2% by weight or less after drying. After the drying process, size-sorting was performed using an ASTM standard testing sieve to obtain a base polymer powder having a particle size of 150 µm to 850 µm.

Meanwhile, for surface crosslinking (additional crosslinking) of the base polymer powder, a surface crosslinking solution containing 4.1 parts by weight of water, 0.5 parts by weight of propylene glycol, and 0.2 parts by weight of 1,3-propanediol, based on 100 parts by weight of the base polymer powder, were mixed and prepared. The surface crosslinking solution was sprayed onto 100 parts by weight of the base polymer using a paddle-type mixer of 1000 rpm. Surface crosslinking was performed by heat treatment at a temperature of 175° C. to 190° C. for 65 minutes to prepare a superabsorbent polymer of Comparative Example 1.

Comparative Example 2

Surface crosslinking was performed in the same manner as in Comparative Example 1 to prepare a superabsorbent polymer. 100 parts by weight of the superabsorbent polymer and 2 parts by weight of sodium benzoate were dry-blended using a Ploughshare mixer to prepare a superabsorbent polymer composition of Comparative Example 2.

Comparative Example 3

Surface crosslinking was performed in the same manner as in Comparative Example 1 to prepare a superabsorbent polymer. 100 parts by weight of the superabsorbent polymer, 0.5 parts by weight of sodium benzoate, and 0.5 parts by weight of EDTA-4Na were dry-blended using a Ploughshare mixer to prepare a superabsorbent polymer composition of Comparative Example 3.

Example 1

A base polymer powder was prepared in the same manner as in Comparative Example 1.

A surface crosslinking solution containing 4.1 parts by weight of water, 0.5 parts by weight of propylene glycol, 0.2 parts by weight of 1,3-propanediol, and 2 parts by weight of sodium benzoate, based on 100 parts by weight of the base polymer powder, were mixed and prepared. The surface crosslinking solution was sprayed onto 100 parts by weight of the base polymer using a paddle-type mixer of 1000 rpm. Thereafter, surface crosslinking was performed by heat treatment at a temperature of 175° C. to 190° C. for 65 minutes to prepare a superabsorbent polymer of Example 1.

Example 2

A base polymer powder was prepared in the same manner as in Comparative Example 1.

A surface crosslinking solution containing 4.1 parts by weight of water, 0.5 parts by weight of propylene glycol, 0.2 parts by weight of 1,3-propanediol, 0.5 parts by weight of sodium benzoate, and 0.5 parts by weight of EDTA-4Na, based on 100 parts by weight of the base polymer powder, were mixed and prepared. The surface crosslinking solution was sprayed onto 100 parts by weight of the base polymer using a paddle-type mixer of 1000 rpm. Thereafter, surface crosslinking was performed by heat treatment at a temperature of 175° C. to 190° C. for 65 minutes to prepare a superabsorbent polymer of Example 2.

Example 3

A base polymer powder was prepared in the same manner as in Comparative Example 1.

A surface crosslinking solution containing 4.4 parts by weight of water, 0.32 parts by weight of ethylene carbonate, 0.32 parts by weight of propylene carbonate, and 2 parts by weight of sodium benzoate, based on 100 parts by weight of the base polymer powder, were mixed and prepared. The surface crosslinking solution was sprayed onto 100 parts by weight of the base polymer using a paddle-type mixer of 1000 rpm. Thereafter, surface crosslinking was performed by heat treatment at a temperature of 175° C. to 190° C. for 65 minutes to prepare a superabsorbent polymer of Example 3.

Example 4

A base polymer powder was prepared in the same manner as in Comparative Example 1.

A surface crosslinking solution containing 4.4 parts by weight of water, 0.32 parts by weight of ethylene carbonate, 0.32 parts by weight of propylene carbonate, 0.5 parts by weight of sodium benzoate, and 0.5 parts by weight of EDTA-4Na, based on 100 parts by weight of the base polymer powder, were mixed and prepared. The surface crosslinking solution was sprayed onto 100 parts by weight of the base polymer using a paddle-type mixer of 1000 rpm. Thereafter, surface crosslinking was performed by heat treatment at a temperature of 175° C. to 190° C. for 65 minutes to prepare a superabsorbent polymer of Example 4.

Example 5

To a 3-L glass reactor equipped with a stirrer and a thermometer, 484 g of acrylic acid, 2100 ppmw of polyethylene glycol diacrylate (PEGDA 400, Mw=400) as an internal crosslinking agent, and 80 ppmw of diphenyl(2,4,6-trimethylbenzoyl)-phosphine oxide as a photoinitiator were added and dissolved, and then 643 g of 31.5 wt % sodium hydroxide solution was added to prepare a water-soluble unsaturated monomer aqueous solution (degree of neutralization: 70 mol %; solid content: 45.8% by weight).

When the temperature of the water-soluble unsaturated monomer aqueous solution increased to 40° C. due to the heat of neutralization, the mixture was put in a container in which 2400 ppmw of sodium persulfate (SPS) as a thermal polymerization initiator and 51.6 g of sodium benzoate (20 wt % aqueous solution) (sodium benzoate: 2 parts by weight, based on 100 parts by weight of acrylic acid) were mixed in advance. Then, UV polymerization was allowed by ultraviolet ray irradiation for 1 minute (UV dose: 10 mV/cm²), and aging was performed by heating in an oven at 80° C. for 120 seconds to obtain a water-containing gel polymer sheet.

The obtained water-containing gel polymer sheet was passed through a chopper having a hole size of 16 mm to prepare crumbs. Then, the crumbs were dried in an oven capable of shifting airflow up and down. The crumbs were uniformly dried by flowing hot air at 185° C. from the bottom to the top for 15 minutes and from the top to the bottom for 15 minutes, such that a water content of the dry product became 2% by weight or less after drying. After the drying process, size-sorting was performed using an ASTM standard testing sieve to obtain a base polymer powder having a particle size of 150 μm to 850 μm.

Meanwhile, for surface crosslinking (additional crosslinking) of the base polymer powder, a surface crosslinking solution containing 4.1 parts by weight of water, 0.5 parts by weight of propylene glycol, and 0.2 parts by weight of 1,3-propanediol, based on 100 parts by weight of the base polymer powder, were mixed and prepared. The surface crosslinking solution was sprayed onto 100 parts by weight of the base polymer using a paddle-type mixer of 1000 rpm. Surface crosslinking was performed by heat treatment at a temperature of 175° C. to 190° C. for 65 minutes to prepare a superabsorbent polymer of Example 5.

Example 6

To a 3-L glass reactor equipped with a stirrer and a thermometer, 484 g of acrylic acid, 2100 ppmw of polyethylene glycol diacrylate (PEGDA 400, Mw=400) as an internal crosslinking agent, and 80 ppmw of diphenyl(2,4,6-trimethylbenzoyl)-phosphine oxide as a photoinitiator were added and dissolved, and then 643 g of 31.5 wt % sodium hydroxide solution was added to prepare a water-soluble unsaturated monomer aqueous solution (degree of neutralization: 70 mol %; solid content: 45.8% by weight).

When the temperature of the water-soluble unsaturated monomer aqueous solution increased to 40° C. due to the heat of neutralization, the mixture was put in a container in which 2400 ppmw of sodium persulfate (SPS) as a thermal polymerization initiator, 13 g of sodium benzoate (20 wt % aqueous solution) (0.5 parts by weight, based on 100 parts by weight of acrylic acid), and 13 g of EDTA-4Na dehydrate (20 wt % aqueous solution) (0.5 parts by weight, based on 100 parts by weight of acrylic acid) were mixed in advance. Then, UV polymerization was allowed by ultraviolet ray irradiation for 1 minute (UV dose: 10 mV/cm$^2$), and aging was performed by heating in an oven at 80° C. for 120 seconds to obtain a water-containing gel polymer sheet.

The obtained water-containing gel polymer sheet was passed through a chopper having a hole size of 16 mm to prepare crumbs. Then, the crumbs were dried in an oven capable of shifting airflow up and down. The crumbs were uniformly dried by flowing hot air at 185° C. from the bottom to the top for 15 minutes and from the top to the bottom for 15 minutes, such that a water content of the dry product became 2% by weight or less after drying. After the drying process, size-sorting was performed using an ASTM standard testing sieve to obtain a base polymer powder having a particle size of 150 μm to 850 μm.

Meanwhile, for surface crosslinking (additional crosslinking) of the base polymer powder, a surface crosslinking solution containing 4.1 parts by weight of water, 0.5 parts by weight of propylene glycol, and 0.2 parts by weight of 1,3-propanediol, based on 100 parts by weight of the base polymer powder, were mixed and prepared. The surface crosslinking solution was sprayed onto 100 parts by weight of the base polymer using a paddle-type mixer of 1000 rpm. Surface crosslinking was performed by heat treatment at a temperature of 175° C. to 190° C. for 65 minutes to prepare a superabsorbent polymer of Example 6.

Evaluation of Physical Properties of Superabsorbent Polymer

Physical properties of the superabsorbent polymers of Examples 1 to 6 and Comparative Examples 1 to 3 were measured by the following methods, and the results are shown in Table 1.

(1) Test of Bacterial Growth-Inhibitory Performance 50 ml of synthetic urine, in which 2500 CFU/ml of *Escherichia coli* (ATCC 25922) was inoculated, was incubated in an oven at 35° C. for 12 hr. This synthetic urine and synthetic urine after incubation for 12 hr were used as a control group, and washed with 150 ml of brine to measure CFU (Colony Forming Unit; CFU/ml), which was determined as the physical property of the control group.

2 g of each superabsorbent polymer of Example or Comparative Example was added to 50 ml of the synthetic urine, in which 2500 CFU/ml of *Escherichia coli* (ATCC 25922) was inoculated, and mixed well by shaking for 1 minute. This mixture was incubated in an oven at 35° C. for 12 hr. The synthetic urine after incubation for 12 hr was washed with 150 ml of brine to measure CFU (Colony Forming Unit; CFU/ml).

Each of the measurement results was calculated as a bacterial inhibition rate (*Escherichia coli*; ATCC25922) represented by the following Equation 1, and based on this, bacterial growth-inhibitory properties of Examples and Comparative Examples were evaluated:

Bacterial inhibition rate=[1−{CFU(12 h)/CFUcontrol (12 h)}]*100(%) [Equation 1]

in Equation 1, CFU (12 h) represents the number of individuals of proliferated bacteria per unit volume of synthetic urine (CFU/ml), which was obtained by adding the superabsorbent polymer to the synthetic urine inoculated with bacteria of *Escherichia coli* (ATCC 25922), and then incubating for 12 hours at 35° C., and CFUcontrol (12 h) represents the number of individuals of proliferated bacteria per unit volume of synthetic urine (CFU/ml), which was obtained by incubating synthetic urine inoculated with bacteria of *Escherichia coli* (ATCC 25922), without the superabsorbent polymer, under the same conditions, i.e., the number of individuals of bacteria of the control group per unit volume of synthetic urine (CFU/ml).

(2) Dust Number

The dust degree of the superabsorbent polymer was analyzed using Dustview II (manufactured by Palas GmbH), measured with a laser. The dust number was measured using 30 g of SAP sample. Since small particles and certain substances fall at a slower rate than coarse grains, the dust number was determined as the value calculated according to Equation 2:

Dust number=Max value+30 sec. value [Equation 2]

in Equation 2, Max value represents the value which is measured at the maximum DUST value when the superabsorbent polymer is dropped into the inlet of the laser dust meter, and 30 sec. value represents the value which is measured for 30 seconds after the Max value is displayed.

(3) Water Retention Capacity (CRC, Centrifugal Retention Capacity)

The water retention capacity by absorption capacity under no load was measured for each superabsorbent polymer in accordance with European Disposables and Nonwovens Association (EDANA) WSP 241.2. After uniformly introducing $W_0$ (g, about 0.2 g) of the superabsorbent polymer in a nonwoven fabric-made bag and sealing the same, it was immersed in 0.9 wt % physiological saline at room temperature. After 30 minutes, the bag was dehydrated by using a centrifuge at 250 G for 3 minutes, and then the weight $W_2$ (g) of the bag was measured. Further, after carrying out the same operation without using the polymer, the weight $W_1$ (g) of the bag was measured.

The water retention capacity was confirmed by calculating CRC (g/g) using the obtained weights according to the following Calculation Formula 1:

CRC (g/g)={[$W_2$ (g)−$W_1$ (g)]/$W_0$ (g)}−1 [Calculation Formula 1]

In Calculation Formula 1, $W_0$ (g) represents the weight (g) of the superabsorbent polymer, $W_1$ (g) represents the weight of the apparatus, which is measured after draining water off at 250 G for 3 minutes using a centrifuge without the superabsorbent polymer, and $W_2$ (g) represents the weight of the apparatus including the superabsorbent polymer, which is measured after immersing the superabsorbent polymer in 0.9 wt % physiological saline solution at room temperature for 30 minutes and draining water off at 250 G for 3 minutes using a centrifuge.

(4) Absorbency Under Pressure (AUP)

The absorbency under pressure (AUP) was measured in accordance with European Disposables and Nonwovens Association (EDANA) WSP 242.2.

First, a 400 mesh stainless steel net was installed in the cylindrical bottom of a plastic having an internal diameter of 60 mm. $W_0$ (g, 0.90 g) of the superabsorbent polymer was uniformly scattered on the steel net under conditions of room temperature and relative humidity of 50%, and a piston capable of uniformly providing a load of 4.83 kPa (0.7 psi) was put thereon, in which an external diameter of the piston was slightly smaller than 60 mm, there was no gap between the internal wall of the cylinder and the piston, and the jig-jog of the cylinder was not interrupted. At this time, the weight $W_3$ (g) of the apparatus was measured.

After putting a glass filter having a diameter of 90 mm and a thickness of 5 mm in a petri dish having a diameter of 150 mm, a physiological saline composed of 0.90 wt % sodium chloride was poured until the surface level of the physiological saline became equal to the upper surface of the glass filter. A sheet of filter paper having a diameter of 90 mm was put thereon. The measurement apparatus was mounted on the filter paper, thereby getting the liquid absorbed under the load for 1 hour. 1 hour later, the weight $W_4$ (g) was measured after lifting the measurement apparatus up.

Absorbency under pressure was confirmed by calculating AUP (g/g) using the obtained weights according to the following Calculation Formula 2:

$$\text{AUP (g/g)} = [W_4 \text{ (g)} - W_3 \text{ (g)}]/W_0 \text{ (g)} \quad \text{[Calculation Formula 2]}$$

in Calculation Formula 2, $W_0$ (g) represents the weight (g) of the superabsorbent polymer, $W_3$ (g) is the total sum of the weight of the superabsorbent polymer and the weight of the apparatus capable of providing a load for the superabsorbent polymer, and $W_4$ (g) is the total sum of the weight of the superabsorbent polymer and the weight of the apparatus capable of providing a load to the superabsorbent polymer, after providing the superabsorbent polymer with water under a load (0.7 psi) for 1 hour.

TABLE 1

|  | Incubation time (hr) | CFU/ml | Bacterial inhibition rate of Equation 1 (%) | CRC (g/g) | AUP (g/g) | Dust number of Equation 2 |
|---|---|---|---|---|---|---|
| Control | 0 | 2500 | — |  |  |  |
|  | 12 | 47,000,000,000 | 0 |  |  |  |
| Comparative Example 1 | 12 | 13,000,000,000 | about 72.3 | 28.5 | 25.7 | 2.2 |
| Comparative Example 2 | 12 | 150,000,000 | about 99.7 | 27.6 | 24.6 | 6.1 |
| Comparative Example 3 | 12 | 180,000,000 | about 99.7 | 27.5 | 24.3 | 10 |
| Example 1 | 12 | 5,300,000 | about 100 | 29.4 | 25.7 | 2 |
| Example 2 | 12 | 14,000,000 | about 100 | 28.6 | 25.9 | 2.1 |
| Example 3 | 12 | 4,000,000 | about 100 | 29.6 | 25.9 | 2.1 |
| Example 4 | 12 | 10,200,000 | about 100 | 29.3 | 25.8 | 2 |
| Example 5 | 12 | 92,000 | about 100 | 29.5 | 23.9 | 2.1 |
| Example 6 | 12 | 1,300,000 | about 100 | 29.1 | 23.8 | 2.2 |

Referring to Table 1, it was confirmed that the superabsorbent polymers of Examples exhibited excellent bacterial growth-inhibitory property and deodorizing property, or low generation of dust while exhibiting no practical deterioration in the water retention capacity and the absorbency under pressure, as compared with those of Comparative Examples.

The invention claimed is:

1. A superabsorbent polymer comprising:
   a base polymer powder including a crosslinked polymer of water-soluble ethylenically unsaturated monomers including acidic groups, of which at least a part is neutralized; and
   a surface-crosslinked layer formed on the surface of the base polymer powder by additionally crosslinking the crosslinked polymer via a surface crosslinking agent,
   wherein the crosslinked polymer of the base polymer powder includes an antimicrobial agent including an organic acid salt having an aromatic ring inside a crosslinked structure thereof,
   wherein the organic acid salt having an aromatic ring is included in an amount of 0.1 part by weight to 5 parts by weight, based on 100 parts by weight of the base polymer powder.

2. The superabsorbent polymer of claim 1, wherein the organic acid salt having an aromatic ring is a sodium (Na) salt or a zinc (Zn) salt of an organic acid having an aromatic ring.

3. The superabsorbent polymer of claim 1, wherein the organic acid salt having an aromatic ring is sodium benzoate or zinc benzoate.

4. The superabsorbent polymer of claim 1, wherein the antimicrobial agent further includes ethylenediaminetetraacetic acid (EDTA) or an alkali metal salt thereof.

5. The superabsorbent polymer of claim 4, wherein the EDTA or alkali metal salt thereof is included in an amount of 0.1 part by weight to 3 parts by weight, based on 100 parts by weight of the base polymer powder.

6. The superabsorbent polymer of claim 1, wherein the surface crosslinking agent includes a diol compound, an alkylene carbonate compound, or a polyvalent epoxy compound.

7. The superabsorbent polymer of claim 1, wherein the superabsorbent polymer has a bacterial inhibition rate (*Escherichia Coli*; ATCC25922) of 75% or more, represented by the following Equation 1:

Bacterial inhibition rate=[1−{CFU(12 h)/CFUcontrol (12 h)}]*100(%)   [Equation 1]

in Equation 1, CFU (12 h) represents a number of individuals of proliferated bacteria per unit volume of synthetic urine (CFU/ml), which was obtained by adding the superabsorbent polymer to synthetic urine inoculated with bacteria of *Escherichia Coli* (ATCC 25922), and then incubating for 12 hours at 35° C., and CFUcontrol (12 h) represents a number of individuals of proliferated bacteria per unit volume of synthetic urine (CFU/ml), which was obtained by incubating synthetic urine inoculated with bacteria of *Escherichia Coli* (ATCC 25922), without the superabsorbent polymer, under the same conditions.

8. The superabsorbent polymer of claim 1, wherein the superabsorbent polymer has a dust number of 1 to 5, as calculated according to the following Equation 2 from results of a laser dust meter:

Dust number=Max value+30 sec. value   [Equation 2]

in Equation 2, Max value represents a value which is measured at a maximum DUST value when the superabsorbent polymer is dropped into an inlet of the laser dust meter, and 30 sec. value represents a value which is measured for 30 seconds after the Max value is displayed.

9. A method of preparing the superabsorbent polymer of claim 1, the method comprising:
   performing crosslinking polymerization of water-soluble ethylenically unsaturated monomers including acidic groups, of which at least a part is neutralized, in the presence of an internal crosslinking agent to form a water-containing gel polymer;
   drying, pulverizing, and size-sorting the water-containing gel polymer to form a base polymer powder; and
   performing additional crosslinking of the base polymer powder by heat treatment in the presence of a surface crosslinking agent,
   wherein the forming the water-containing gel polymer or the performing additional crosslinking is performed in the presence of an antimicrobial agent containing an organic acid salt having an aromatic ring.

10. The method of claim 9, wherein, during the forming the water-containing gel polymer, crosslinking polymerization of a monomer aqueous solution including the water-soluble ethylenically unsaturated monomers, a polymerization initiator, the internal crosslinking agent, and the antimicrobial agent is performed.

11. The method of claim 9, wherein the performing additional crosslinking is performed by using a surface crosslinking solution including the surface crosslinking agent and the antimicrobial agent.

12. The method of claim 9, wherein the organic acid salt having an aromatic ring is included in an amount of 0.1 part by weight to 5 parts by weight, based on 100 parts by weight of the water-soluble ethylenically unsaturated monomers or the base polymer powder.

13. The method of claim 9, wherein the antimicrobial agent further includes EDTA or an alkali metal salt thereof.

14. The method of claim 13, wherein the EDTA or alkali metal salt thereof is used in an amount of 0.1 part by weight to 3 parts by weight, based on 100 parts by weight of the water-soluble ethylenically unsaturated monomers or the base polymer powder.

15. A hygienic product comprising the superabsorbent polymer of claim 1.

* * * * *